US00PP18989P2

(12) United States Plant Patent
Hemmett

(10) Patent No.: US PP18,989 P2
(45) Date of Patent: Jun. 24, 2008

(54) *DAHLIA* PLANT NAMED 'SCARLET FERN'

(50) Latin Name: *Dahlia variabilis*
Varietal Denomination: Scalet Fern

(76) Inventor: Keith Hemmett, 488 C Dan Buck Road, Auckland 1008 (NL)

( * ) Notice: Subject to any disclaimer, the term of this patent is extended or adjusted under 35 U.S.C. 154(b) by 0 days.

(21) Appl. No.: 11/501,642

(22) Filed: Aug. 8, 2006

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent L Bell
*Assistant Examiner*—June Hwu

(57) ABSTRACT

A new cultivar of *Dahlia* named 'SCARLET FERN' that is distinguishable by upright habit, mahogany-black divided leaves, and orange-red star-shaped blossoms. In combination these traits set 'SCARLET FERN' apart from all other existing varieties of *Dahlia* known to the inventor.

2 Drawing Sheets

Genus: *Dahlia.*
Species: *variabilis.*
Denomination: 'SCARLET FERN'.

BACKGROUND OF THE INVENTION

The present invention relates to a new and distinct cultivar of *Dahlia* grown for use in mixed combinations, beds and the landscape. The new invention is known botanically as *Dahlia variabilis* and will be referred to hereinafter by the cultivar name 'SCARLET FERN'. The specific epithet *variabilis* represents a hybrid seedling line that came from crossing various original wild species in the early 1800's, and refers to the species' wide range of flower color and shapes. *Dahlia* is in the family Compositae. The flower of 'SCARLET FERN' is a "single" form blossom and exhibits a single row of ray flowers surrounding a central cluster of disk florets.

'SCARLET FERN' was selected as a seedling that resulted from the controlled cross-pollination carried out by the inventor in a cultivated area of Auckland, New Zealand. The breeding began in 1999 by crossing an individual plant *Dahlia variabilis* 'Roxy' (unpatented) as the female parent and an individual of *Dahlia variabilis* 'Razzmatazz' (unpatented) as the male parent. Seed was collected from the female parent and coded as 71152, then sown with the intention of making a selection from the seedlings that resulted.

'SCARLET FERN' was selected in 2000 based on the criteria of leaf color, and shape, plant height, and flower color. Selection was conduced by the inventor, in Auckland, New Zealand. The unique traits that distinguish the new *Dahlia* variety named 'SCARLET FERN' from other varieties of *Dahlia* known to the inventor are mahogany-black divided leaves and profusions of vivid orange-red star-shaped blossoms. The new *Dahlia* named 'SCARLET FERN' is distinguishable from the parents by height, leaf shape and color, and flower color.

'SCARLET FERN' can be distinguished from other *Dahlia* cultivars with dark foliage by its size, type of flower, and color of leaves. When compared to 'Redskin', 'SCARLET FERN' is twice the size in height and width. 'Redskin' has double flowers whereas 'SCARLET FERN' has single blooms. The foliage of 'SCARLET FERN' is a darker, almost black color compared to the lighter maroon/green foliage of 'Redskin'. When compared to 'Bishop's Children', 'SCARLET FERN' is bigger in size. At maturity, it is 36" by 36" compared to 'Bishop's Children' which reaches a height and width of 24" by 12". The flowers of 'SCARLET FERN' are stable in color and form whereas 'Bishop's Children' vary from plant to plant in color and form.

'SCARLET FERN' exhibits upright habit, large grey-orange buds, fragrant orange-red flowers, mahogany-black foliage, and brown stems. The large star-shaped blossoms bloom in summer and fall. Cultural conditions include full sun, regular water and rich well-draining potting soil. 'SCARLET FERN' is hardy is USDA Zone 8 and grows to 0.9 m in height and 0.9 m in width at maturity.

The first asexual reproduction of 'SCARLET FERN' was conducted in 2004 in Auckland, New Zealand. The method of asexual propagation utilized was tissue culture. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'SCARLET FERN'. These traits in combination distinguish 'SCARLET FERN' from all other existing varieties of *Dahlia* known to the inventor. 'SCARLET FERN' has not been tested under all possible conditions and phenotypic differences may be observed with variations in environmental, climatic, and cultural conditions, however, without any variance in genotype.

1. 'SCARLET FERN' exhibits upright habit.
2. 'SCARLET FERN' exhibits mahogany-black divided leaves.
3. 'SCARLET FERN' is grown for use in mixed combinations, beds and the landscape.
4. 'SCARLET FERN' exhibits large grey-orange buds and brown stems.

5. 'SCARLET FERN' exhibits fragrant orange-red star-shaped blossoms.
6. 'SCARLET FERN' blooms summer and fall.
7. 'SCARLET FERN' grows to 0.9 m in height and 0.9 m in width at maturity.
8. 'SCARLET FERN' is hardy to USDA Zone 8.

BRIEF DESCRIPTION OF THE DRAWINGS

The accompanying color drawings labeled

The drawings labeled FIG. 1 depicts the entire plant in bloom from a side perspective.

The drawing labeled FIG. 2 depicts a close-up view of the flowers. Drawings were made using conventional techniques and although flower and foliage color may appear different from actual color due to light reflectance, they are as accurate as possible by conventional photography.

BOTANICAL DESCRIPTION OF THE PLANT

Figure 1:
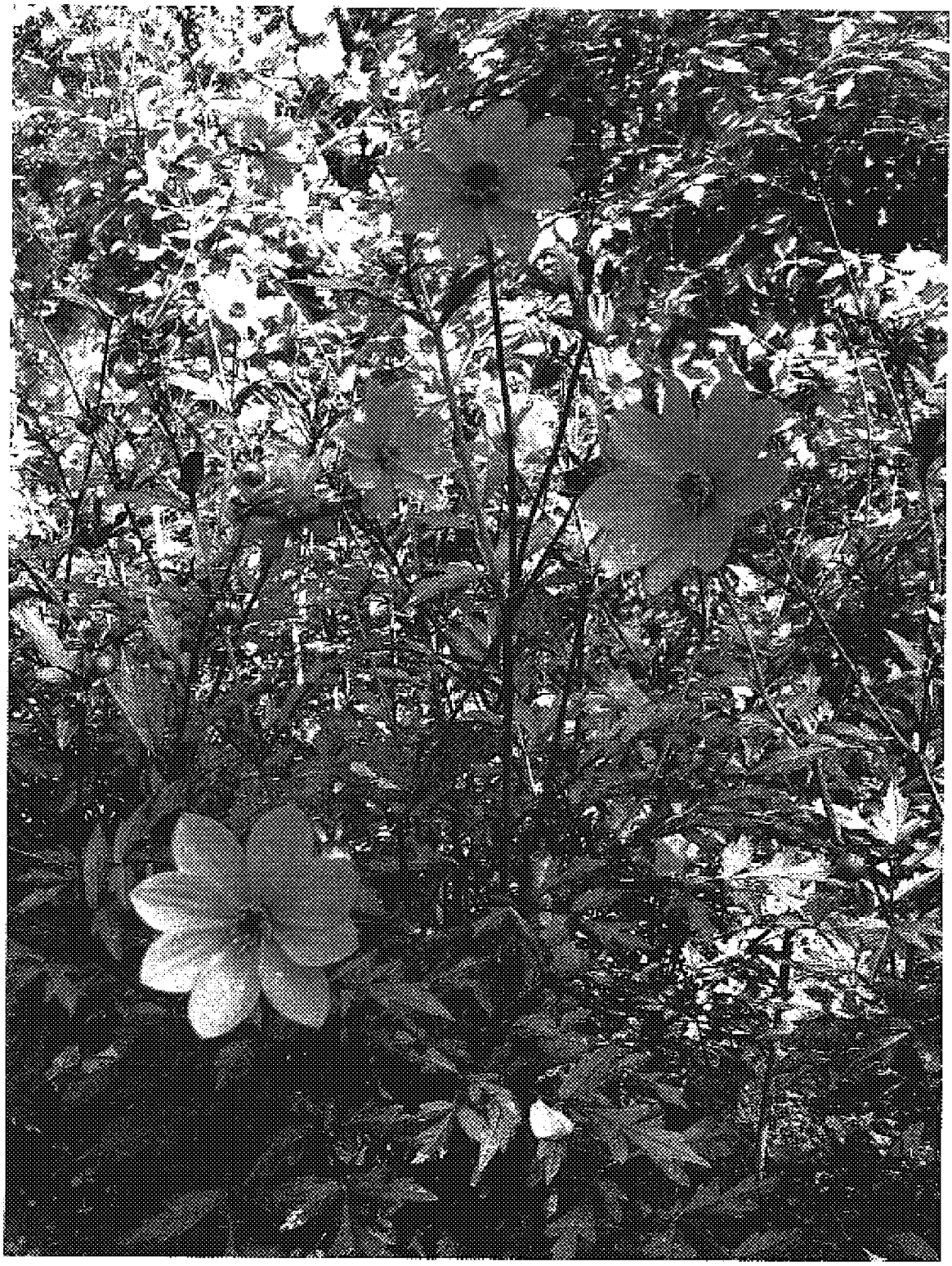
FIG. 1 and FIG. 2 illustrate the overall appearance of the new *Dahlia* cultivar named 'SCARLET FERN' showing the colors as true as is reasonably possible to obtain in colored reproductions of this type. Colors in the photographs may differ from the color values cited in the detailed botanical description, which accurately describes the actual colors of the new *Dahlia* variety named 'SCARLET FERN'.
Figure 2:
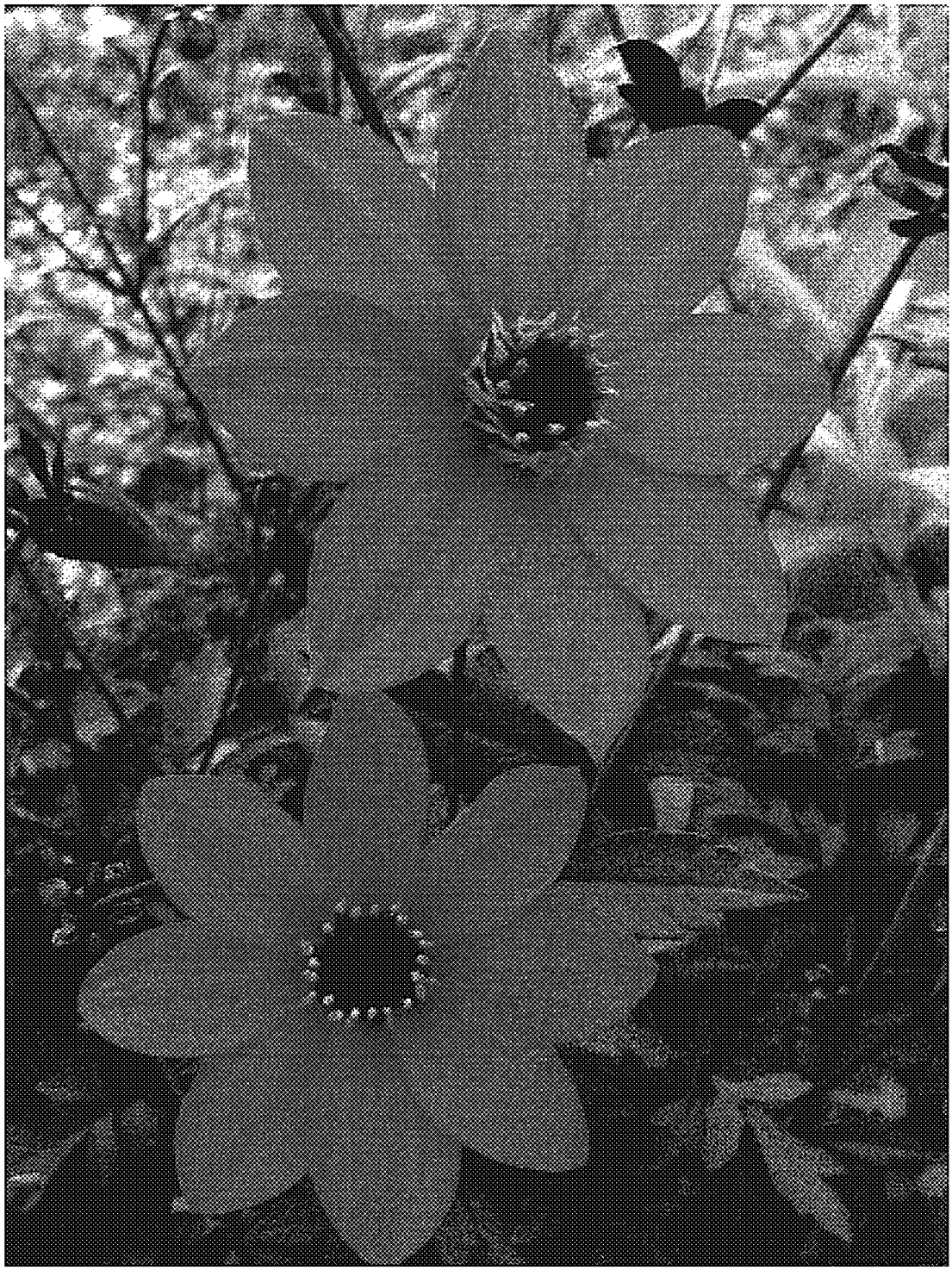

The following is a detailed botanical description of the new *Dahlia* cultivar named 'SCARLET FERN'. Observations, measurements, values and comparisons were collected in Arroyo Grande, Calif. from 2-litre container plants. Color determinations were made in accordance with The 2001 Royal Horticultural Society Colour Chart from London England, except where general color terms of ordinary dictionary significance are used. Growing requirements are similar to the species.

Botanical classification: *Dahlia variabilis* 'SCARLET FERN'.
Family: Compositae.
Genus: *DAHLIA*.
Species: *variabilis*.
Denomination: 'SCARLET FERN'.
Common name: *Dahlia*.
Parentage: *Dahlia variabilis* 'SCARLET FERN' is a seedling that resulted from the controlled cross-pollination of the following parents:
*Female parent.*—*Dahlia variabilis* 'Roxy'.
*Male parent.*—*Dahlia variabilis* 'Razzmatazz'.
Propagation method: Tissue culture.
Rooting system: Fine and fibrous.
Vigor: Vigorous.
Habit: Upright habit.
Use: For use in mixed combinations, beds and the landscape.
Type: Perennial.
Dimensions in first season: 0.6 m in height and 0.6 m in width.
Demensions at maturity: 0.9 m in height and 0.9 m in width.
Cultural requirements: Grow in full sun with regular water, and well-draining potting soil.
Pest susceptibility: Susceptible to aphids.
Disease susceptibility: Susceptible to powdery mildew in highly humid conditions.
Hardiness: USDA Zone 8.

Stem:
*Color.*—200B.
*Dimensions.*—40 cm in length and 0.4 cm in width.
*Shape.*—Cylindrical.
*Surface.*—Glabrous.
*Internode length* (*average*).—7 cm.

Foliage:
*Leaf arrangement.*—Opposite.
*Leaf division.*—Simple.
*Margin.*—Ciliate and pinnatisect.
*Leaf shape.*—Hastate.
*Leaf dimensions* (*average*).—9 cm in length and 8.50 cm in width.
*Leaf base.*—Attenuate.
*Leaf apex.*—Acute.
*Leaf venation pattern.*—Pinnate.
*Vein color* (*abaxial and adaxial surfaces*).—N186C.
*Leaf surfaces* (*abaxial and adaxial surfaces*).—Slightly puberulent.
*Leaf color* (*adaxial surface*).—N186A.
*Leaf color* (*abaxial surface*).—189A.
*Leaf attachment.*—Petiolate.
*Petiole shape.*—Sulcate.
*Petiole dimensions.*—2.50–4 cm in length and 0.10 cm in width.
*Petiole color.*—N186B.
*Presence of stipules or spines.*—None observed.
*Leaf fragrance.*—None observed.

Inflorescence:
*Inflorescence type.*—Head.
*Aspect.*—Facing upward and outward.
*Inflorescence quantity.*—15–20 per 2-litre container plant.
*Dimensions of inflorescence* (*average*).—9.50 cm in diameter and 5 cm in depth.
*Inflorescence shape.*—Radiate with center disc.
*Blooming seasons.*—Summer and fall.
*Peduncle.*—Dimensions (average): 17 cm in length and 0.25 cm in diameter. Shape: Cylindrical. Surface: Glabrous. Color: 200B.
*Bud.*—Shape: Oblate. Dimensions (average): 1.25 cm in height and 1.50 cm in diameter. Surface: Glabrous. Appearance: Semi-glossy. Color: 165A. Apex: Obtuse. Base: Truncate.
*Ray floret.*—Dimensions (average): 5 cm in length and 2.25 cm in width. Shape: Oval. Surface (adaxial and abaxial): Glabrous. Flower arrangement: Radiate. Quantity per inflorescence: 8 per inflorescence. Apex: Rounded. Base: Rounded. Margin: Entire. Color (adaxial and abaxial surfaces): 33A. Vein color (adaxial and abaxial surfaces): 35D. Vein pattern: Parallel.
*Disk floret.*—Average diameter of disk: 1.5 cm. Dimensions: 2 cm in length and 0.10 cm in width. Quantity of disk florets: In excess of 90 disk florets per inflorescence. Color: 187A. Disc florets: 5 in number fused into a tubular corolla. Disc florets fused or unfused: Fused. Disc floret: Acute. Disc floret surface (ventral and dorsal surfaces): Glabrous. Receptacle dimensions: 1 cm in depth and 1.50 cm in diameter. Receptacle surface: Glabrous. Receptacle color: 187A.
*Phyllary.*—Inner phyllary: Number: 8. Shape: Elongated ovate. Dimensions: 2 cm in length and 1 cm in width. Color (adaxial and abaxial surfaces): 162A. Texture: Scarious. Appearance: Translucent. Apex:

Subacute. Base: Truncate. Margin: Entire. Surface (adaxial and abaxial): Glabrous. Outer phyllary: Number: 5. Shape: Obovate. Dimensions: 1.50 cm in length and 0.60 cm in width. Color (adaxial and abaxial surfaces): N187A and N189A both observed. Form: Reflexed. Apex: Obtuse. Base: Truncate. Margin: Entire. Surface (adaxial and abaxial): Glabrous.

*Self-cleaning or persistent.*—Self-cleaning.

*Fragrance of inflorescence.*—Perfume fragrance.

Reproductive organs:

*Location.*—Disk florets.

*Stamens.*—5 in number.

*Stamen attachment.*—Filament adnate to ventral surface of corolla.

*Stamen length.*—6 mm. in length.

*Stamen color.*—166A.

*Anther.*—Connate.

*Anther color.*—166A.

*Pollen.*—Present.

*Quantity of pollen.*—Large amount.

*Pollen color.*—N163D.

*Pistil.*—One present.

*Pistil length.*—9 mm in length.

*Stigma dimensions.*—6 mm in length and 6 mm in width.

*Stigma form.*—Plumose.

*Stigma color.*—N163C.

*Stigma shape.*—Bifurcate.

*Ovary position.*—Inferior.

*Ovary color.*—150D.

*Ovary shape.*—Rotund.

*Ovary dimensions.*—2 mm in width and 3 mm in height.

Seed: None observed to date.

What is claimed is:

1. A new and distinct cultivar of *Dahlia* plant named 'SCARLET FERN', as described and illustrated herein within.

* * * * *